United States Patent [19]

Singh et al.

[11] Patent Number: 5,840,908
[45] Date of Patent: Nov. 24, 1998

[54] SULFENAMIDE ACCELERATORS AND RUBBER COMPOSITIONS CONTAINING THE SAME

[75] Inventors: Balwant Singh; Thomas Patrick Sassi, both of Stamford; Laurence Wu-Kwang Chang, Orange, all of Conn.

[73] Assignee: Cytec Technology Corp., Wilmington, Del.

[21] Appl. No.: 239,676

[22] Filed: May 9, 1994

[51] Int. Cl.⁶ .................................................. C07D 277/80
[52] U.S. Cl. ............................................ 548/164; 548/168
[58] Field of Search ...................... 548/167, 168

[56] References Cited

U.S. PATENT DOCUMENTS

| | | | |
|---|---|---|---|
| 2,321,305 | 6/1943 | Messer | 260/788 |
| 2,321,306 | 6/1943 | Messer | 268/306.6 |
| 2,762,814 | 9/1956 | Lunt | 260/306.6 |
| 2,860,142 | 11/1958 | Conly | 260/306.6 |
| 2,873,277 | 2/1959 | Sundholm | 260/206.6 |
| 2,889,331 | 6/1959 | Sundholm | 260/306.6 |
| 3,221,087 | 11/1965 | Harman | 264/144 |
| 3,549,650 | 12/1970 | D'Amico | 260/306.6 |
| 3,595,871 | 7/1971 | Campbell et al. | 260/306.6 |
| 3,875,177 | 4/1975 | Maison | 260/306.6 |
| 4,439,616 | 3/1984 | Singh et al. | 560/25 |
| 5,096,978 | 3/1992 | Coran | 525/346 |

FOREIGN PATENT DOCUMENTS

| | | |
|---|---|---|
| 176039 B1 | 1/1979 | Czech Rep. . |
| 176040 B1 | 1/1979 | Czech Rep. . |
| WO92/05218 | 4/1992 | WIPO . |

OTHER PUBLICATIONS

E. Morita, "S–N Compounds as Delayed Action Chemicals In Vulcanization", *Rubber Chemistry and Technology,* 53, pp. 393–436, (1980).

Gögh et al., "Relations Between the Structure and Vulcanization Characteristics of N–Substituted 2–Benzotriazole Sulfenamides," *Plasty Kauc,* 26 (10), pp. 301–307 (1989). (Transalation).

E. Morita et al., "Rubber Chemicals From Cyclic Amines, II Dithioamines and Sulfenamides as Accelerators and Curing Agents", *Rubber Chemistry and Technology,* 50(5), pp. 720–735, (1977).

PCT Search Report for International Application No. PCT/US95/04767 dated Sep. 6, 1995.

CA 106(5): 33035a (1987).

CA 91(6): 40741C (1979).

CA 112(26): 23670n (1990).

Carr et al. "Thiazolesulfenamides", *J. Organic Chemistry,* 14, pp. 921–934, (1949).

Tori, et al. "Electrosynthesis of Hetero–Hetero Atom Bonds", *J. Organic Chemistry,* 43, pp. 3223–3227, (1978).

Davies et al., "The Impact of N–Nitrosamine Regulations on Sulphenamide Selection", *Kautschuk und Gummi Kunstsoffe* 42, pp. 121–123, (1989).

J.J. D'Amico etal., "Derivatives of Thiazolethiols", *Journal of American Chemical Society,* 79, pp. 5270–5276, (1957).

Kharasch etal., "The Sulfenic Acids and Their Derivatives", *Chemical Reviews,* 39, pp. 269–323, (1946).

*Primary Examiner*—Johann Richter
*Assistant Examiner*—Lauro R. C. Lutz
*Attorney, Agent, or Firm*—Pennie & Edmonds

[57] ABSTRACT

Novel mono- and bis-benzothiazole sulfenamide compounds based on primary amines are provided which may be employed as rubber vulcanization accelerators having excellent scorch safety. Vulcanizable rubber compositions containing rubber, sulfur and the novel benzothiazole sulfenamide compounds are also provided.

17 Claims, No Drawings

SULFENAMIDE ACCELERATORS AND RUBBER COMPOSITIONS CONTAINING THE SAME

BACKGROUND OF THE INVENTION

1. Field of the Invention

This invention relates generally to certain novel benzothiazole sulfenamide derivatives based on hindered primary amines, and their use as non-nitrosamine generating accelerators in rubber compositions. More specifically, the present invention relates to certain at least dialkyl substituted cyclohexylamine, and certain α-substituted benzylamine, derived sulfenamide compounds which provide excellent scorch safety when so utilized.

2. Description of Related Art

2-Mercaptobenzothiazole sulfenamides have long been used as vulcanization accelerators by the rubber industry. They provide relatively long scorch safety or processing margin, i.e., the time during which the vulcanization mixture can be processed before crosslinking or vulcanization commences, allowing for faster processing at higher temperatures.

U.S. Pat. No. 2,321,305 and PCT International Publication No. WO92/05218 disclose certain benzothiazole mono- and bis-sulfenamide accelerators derived from branched, linear, cycloalkyl or arylamines, such as isopropyl, isobutyl, cyclohexyl, t-butyl, t-amyl, t-octyl, benzyl and dibenzylamines. Bis- and tris-sulfenamides derived from ammonia and mercaptobenzothiazole disulfide are disclosed by U.S. Pat. No. 2,321,306. Alternate processes to manufacture N-alkyl and N-cycloalkyl bis(2-benzothiazole)sulfenamides are disclosed in U.S. Pat. Nos. 2,860,142, 2,873,277, 2,889,331 and 3,875,177.

The sulfenamides may, for example, be produced by oxidatively coupling 2-mercaptobenzothiazole with a primary or a secondary amine. Examples of known sulfenamide accelerators include, for example, 2-(4-morpholinylthio)benzothiazole ("MBS"), N,N-di-isopropyl-2-benzothiazole sulfenamide ("DIBS"), N-t-butyl-2-benzothiazole sulfenamide ("TBBS"), N,N-dicyclohexyl-2-benzothiazole sulfenamide ("DCBS"), N-t-butylbis(2-benzothiazole sulfen)amide ("TBSI"), 2-(4-morpholinyldithio)benzothiazole("MBDS"), N-cyclohexyl-2-benzothiazole sulfenamide ("CBS").

Secondary amine based accelerators, such as MBS, provide an excellent overall balance of scorch safety and cure rate, which is highly desirable. However, secondary amines produce stable nitrosamines which have been the subject of environmental criticism. It is generally accepted that nitrosamines are formed by the reaction of the secondary amino groups with nitrosating agents derived from oxides of nitrogen and/or the nitrites. On the other hand, it is known that primary amines produce unstable nitrosamines; the nitroso structures rearrange to diazonium hydroxides which readily decompose to the corresponding alcohols, nitrogen and water.

The two most commonly used primary amine based sulfenamides are TBBS and CBS. Both are deficient in scorch safety relative to the morpholine derivative, MBS, which is known to exhibit a highly desirable level of scorch safety.

It has been suggested by Davies, K. M., et al., "The Impact of N-Nitrosamine Regulations on Sulfenamide Selection," *Kautschuk und Gummi Kunststoffe,* Vol. 42, pp. 120–23 (1989), that primary amine based sulfenamides, such as N-t-amyl-2-benzothiazole sulfenamide ("TABS") or N-t-octyl-2-benzothiazole sulfenamide ("TDBS") could be used to replace MBS to overcome the release of nitrosamines. However, it is noted that TABS and TDBS, which have long been known, are not commercially available because they are costly to produce.

Czech Patent Nos. 176040 and 176039 disclose, respectively, N-2-methylcyclohexylbenzothiazole sulfenamide and its use as a vulcanization accelerator which provides improved dynamic properties to vulcanized rubber compositions. However, Czech Patent No. 176039 discloses that the scorch safety of N-2-methylcyclohexylbenzothiazole sulfenamide is only comparable to that of TBBS and CBS.

Gogh, J., et al., "Relations Between the Structure and Vulcanization Characteristics of N-Substituted 2-Benzothiazole Sulfenamides," *Plasty Kauc.,* Vol. 26 (10), pp. 301–7 (1989) reports that scorch safety rises, while vulcanization rate falls as the steric environment of the amine group of a benzothiazole sulfenamide increases. This reference concludes that while the most favorable sulfenamide accelerators will have a large scorch safety and a high vulcanization rate, the achievement of such ideal properties is limited due to the contradictory nature of scorch safety and vulcanization rate, i.e., the higher the scorch safety the lower the vulcanization rate and vice versa.

It is known that the scorch safety of CBS and TBBS can be improved by incorporating low levels (0.1–0.2 Wt %) of a cure retarder such as N-(cyclohexylthio)phthalimide (available from Monsanto Company under its trademark Santogard® PVI). However, the use of a cure retarder requires careful balancing of the formulations to avoid unacceptable cure rates and/or changes in rubber moduli. It is also known that substituted urea coactivators can be combined with sulfenamide accelerators to provide improved properties of scorch delay and cure rate in synthetic rubber compositions as disclosed in U.S. Pat. No. 5,096,978. Such coactivators, however, were found to have little effect on natural rubber compositions.

All of the aforementioned references are incorporated by reference herein for all purposes as if fully set forth.

It has now been unexpectedly found that certain dialkyl substituted cyclohexylamine and α-substituted benzylamine derived sulfenamides provide substantially improved scorch safety relative to CBS and TBBS, and approaching that of the morpholine derivative MBS, without the use of external retarders, and without the generation of stable nitrosamines.

SUMMARY OF THE INVENTION

As indicated above, the present invention is directed to novel benzothiazole sulfenamide compounds and their use as vulcanization accelerators. In their broadest aspects, the novel benzothiazole sulfenamide compounds in accordance with the invention are represented by the Formula (I)

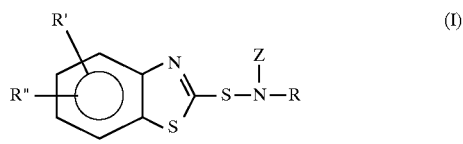

wherein Z is selected from the group consisting of hydrogen and a sulfobenzothiazole group represented by the Formula (II)

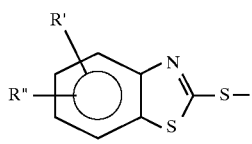

(II)

wherein each R' and R" is independently selected from the group consisting of hydrogen and $C_1$–$C_6$ alkyl; and wherein R is selected from the group consisting of groups represented by the Formulae (i) and (ii)

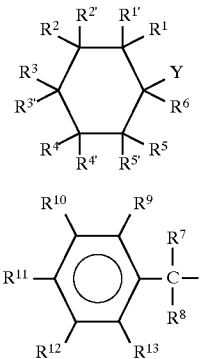

wherein in Formula (i)
  Y is optional and, when present, is a group of the formula —[($R^{14}$)($R^{15}$)C]—, wherein $R^{14}$ and $R^{15}$ are independently selected from the group consisting of hydrogen and $C_1$–$C_6$ alkyl,
  $R^1$, $R^{1'}$, $R^2$, $R^{2'}$, $R^3$, $R^{3'}$, $R^4$, $R^{4'}$, $R^5$, $R^{5'}$ and $R^6$ are each independently selected from the group consisting of hydrogen and $C_1$–$C_6$ alkyl, with the proviso that at least two of $R^1$ through $R^6$ are $C_1$–$C_6$ alkyl, and with the proviso that one of $R^2$, $R^{2'}$, $R^3$, $R^{3'}$, $R^4$ or $R^{4'}$ may optionally further be selected from a group of the Formula (iii)

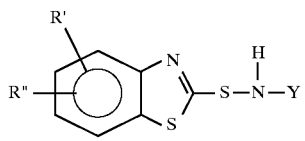

wherein R', R" and Y are independently as defined above; and wherein in the Formula (ii)
  $R^7$ is a $C_1$–$C_6$ alkyl,
  $R^8$ is selected from the group consisting of hydrogen and $C_1$–$C_6$ alkyl, and $R^9$, $R^{10}$, $R^{11}$, $R^{12}$ and $R^{13}$ are each independently selected from the group consisting of hydrogen and $C_1$–$C_6$ alkyl, with the proviso that one of $R^{10}$, $R^{11}$ or $R^{12}$ may optionally further be selected from a group consisting of $CH_2$=CH—, $CH_2$=C($CH_3$)—, $CH_2$=CH—$CH_2$—, $CH_2$=C($CH_3$)$CH_2$—, and a group of the formula (iii).

This invention is further directed to vulcanizable rubber compositions comprising rubber, sulfur and, as vulcanization accelerator, the benzothiazole sulfenamide compounds described above. The invention is also directed to a process for preparing a cured rubber article by vulcanizing rubber and sulfur in the presence, as vulcanization accelerator, of the benzothiazole sulfenamide compounds described above. Advantageously, the benzothiazole sulfenamide compounds of this invention, when so utilized, provide excellent scorch safety without generating stable nitrosamines during the vulcanization of rubber compositions.

These and other features and advantages of the present invention will be more readily understood by those of ordinary skill in the art from a reading of the following detailed description.

DETAILED DESCRIPTION OF THE PREFERRED EMBODIMENTS

The novel benzothiazole sulfenamide compounds of this invention are mono-, bis- and tris-benzothiazole sulfenamide compounds as represented by the general Formula (I) above. Preferred for the present invention are those benzothiazole sulfenamide compounds represented by the Formula (I), wherein all R' and R" groups are hydrogen.

A first preferred embodiment of the present invention is directed to the mono-benzothiazole sulfenamide compounds, wherein Z=H, and bis-benzothiazole sulfenamide compounds, wherein Z=the sulfobenzothiazole group (II), and further wherein R is the group represented by the Formula (iv)

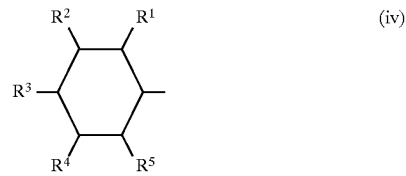

wherein $R^1$, $R^2$, $R^3$, $R^4$ and $R^5$ are independently selected from the group consisting of hydrogen and $C_1$–$C_6$ alkyl, with the proviso that at least two of $R^1$ through $R^5$ are $C_1$–$C_6$ alkyl.

More preferred are those wherein $R^1$, $R^2$, $R^3$, $R^4$ and $R^5$ are independently selected from hydrogen and methyl, provided that at least two of $R^1$ through $R^5$ are methyl. Especially preferred is when $R^1$ is methyl and one of either $R^2$, $R^3$, $R^4$ or $R^5$ is also methyl.

As specific examples of mono-benzothiazole sulfenamide compounds of this first preferred embodiment may be mentioned N-(2,3-dimethylcyclohexyl)-2-benzothiazole sulfenamide, N-(2,4-dimethylcyclohexyl)-2-benzothiazole sulfenamide, N-(2,5,-dimethylcyclohexyl)-2-benzothiazole sulfenamide and N-(2,6-dimethylcyclohexyl)-2-benzothiazole sulfenamide. As specific examples of bis-benzothiazole sulfenamide compounds of this first preferred embodiment may be mentioned N-(2,3-dimethylcyclohexyl) bis(2-benzothiazole sulfen)amide, N-(2,4-dimethylcyclohexyl)bis(2-benzothiazole sulfen)amide, N-(2,5-dimethylcyclohexyl)bis(2-benzothiazole sulfen) amide and N-(2,6-dimethylcyclohexyl)bis(2-benzothiazole sulfen)amide.

A second preferred embodiment of the present invention is directed to the mono-benzothiazole sulfenamide compounds, wherein Z=H, and bis-benzothiazole sulfenamide compounds, wherein Z=the sulfobenzothiazole group (II), and further wherein R is a group represented by the Formula (v)

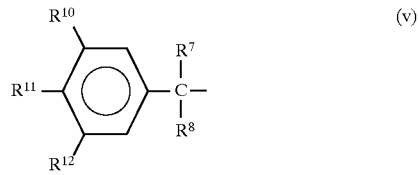

wherein $R^7$ is a $C_1$–$C_6$ alkyl, $R^8$ is selected from the group consisting of hydrogen and $C_1$–$C_6$ alkyl, and $R^{10}$, $R^{11}$ and $R^{12}$ are hydrogen, with the proviso that one of $R^{10}$, $R^{11}$ or $R^{12}$ may optionally be selected from the group consisting of hydrogen, $CH_2$=CH—, $CH_2$=C($CH_3$)—, $CH_2$=CH—$CH_2$— and $CH_2$=C($CH_3$)$CH_2$—.

More preferred are those wherein $R^7$ is methyl, $R^8$ is selected from the group consisting of hydrogen and methyl, and two of $R^{10}$, $R^{11}$ and $R^{12}$ are hydrogen and the other is selected from the group consisting of hydrogen and isopropenyl.

As specific examples of mono-benzothiazole sulfenamide compounds of this second embodiment may be mentioned N-(α-methylbenzyl)-2-benzothiazole sulfenamide, N-(α,α-dimethylbenzyl)-2-benzothiazole sulfenamide, N-(3-isopropenyl-α,α-dimethylbenzyl)-2-benzothiazole sulfenamide, and N-(4-isopropenyl-α,α-dimethylbenzyl)-2-benzothiazole sulfenamide. As specific examples of bis-benzothiazole sulfenamide compounds of the second embodiment may be mentioned N-(α-methylbenzyl)bis (2benzothiazole sulfen)amide, N-(α,α-dimethylbenzyl)bis (2-benzothiazole sulfen)amide, N-(3-isopropenyl-α,α-dimethylbenzyl)bis(2-benzothiazole sulfen)amide, and N-(4-isopropenyl-α,α-dimethylbenzyl)bis(2-benzothiazole sulfen)amide.

A third preferred embodiment of the present invention is directed to the bis-benzothiazole sulfenamide compounds, wherein Z is H, R is the group represented by formula (v), and two of $R^{10}$, $R^{11}$ and $R^{12}$ are hydrogen and the other is represented by a group of the formula (vi)

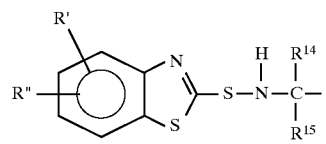

(vi)

wherein $R^{14}$ is a $C_1$–$C_6$ alkyl, more preferably methyl, $R^{15}$ is selected from the group consisting of hydrogen and $C_1$–$C_6$ alkyl, more preferably hydrogen and methyl, and R' and R" are as previously defined.

As specific examples of this third preferred embodiment may be mentioned α,α,α',α'-tetramethyl-para-xylylene di(benzothiazole sulfenamide) and α,α,α',α'-tetramethyl-meta-xylylene di(benzothiazole sulfenamide).

The benzothiazole sulfenamide derivatives of this invention may be prepared from the appropriate starting materials by well-known procedures described generally in various of the previously incorporated references. As one example may be mentioned the oxidative coupling of 2-mercaptobenzothiazole, which is a well known and readily available starting material, with the appropriate primary mono- or diamine.

For example, in the first preferred embodiment, the appropriate amine is a dimethyl substituted cyclohexylamine derivatives where the methyl groups are preferably in the 2,3-, 2,4-, 2,5- and 2,6- positions relative to the amine group. Such amines are commercially available or are easily prepared.

In the second preferred embodiment, the appropriate amines include, for example, α-methylbenzylamine ("phenethylamine"), α,α-dimethylbenzylamine, and alkyl or vinyl substituted derivatives of α,α,α,α-tetramethylxylylene diamine, which may be obtained via hydrolysis of the corresponding isocyanates and/or the carbamates. Such isocyanates and carbamates may be prepared based on the procedures set forth in U.S. Pat. No. 4,439,616, the disclosure of which is incorporated by reference herein for all purposes as if fully set forth.

In the third preferred embodiment, the appropriate amines include, for example, α,α,α,α-tetramethylxylylene diamines, which may also be obtained via hydrolysis of the corresponding isocyanates and/or the carbamates as just described.

As indicated above, the benzothiazole sulfenamide compounds of the present invention can be readily prepared from the appropriate starting materials by procedures generally well-known to those of ordinary skill in the art (as described in various of the previously incorporated reference, as illustrated by the examples as set forth below. For example, the bis-benzothiazole sulfenamide compounds of the present invention may be prepared by conversion of the monobenzothiazole sulfenamide compounds of this invention in accordance with the procedure of previously incorporated U.S. Pat. No. 2,860,142.

The benzothiazole sulfenamide compounds of the present invention are particularly useful for crosslinking natural or synthetic rubber elastomers. Examples of elastomers which may be utilized are the diene polymers based on 1,3-butadiene ("butadiene"), 2-methyl-1,3-butadiene ("isoprene"), 1,3-pentadiene, 2,3-dimethyl-1,3-butadiene and their copolymers with styrene, α-methylstyrene, acrylonitrile, methacrylonitrile, methyl acrylate, ethyl acrylate, butyl acrylate, methyl methacrylate, ethyl methacrylate, vinyl acetate and the like. Preferred highly unsaturated elastomers include natural rubber, cis-polyisoprene, polybutadiene, poly(styrene-butadiene), polychloroprene and poly(acrylonitrile-butadiene). Mixtures of rubbers with other elastomers such as ethylenepropylene-diene ("EPDM"), ethylenepropylene rubber ("EPR"), hydrogenated butyl rubber, butyl rubber and EPDM polymers made from ethylene, propylene and a non-conjugated diene may also be used. The EPDM polymers alone are less preferred.

This invention is also directed to vulcanizable rubber compositions containing natural rubber, synthetic rubber or mixtures thereof, elemental sulfur and, as vulcanization accelerator, the benzothiazole sulfenamide compounds of this invention. The amount of sulfur used is that amount which will vulcanize the rubber, and generally ranges from about 0.25 to about 4 parts per hundred parts of rubber (phr). The preferred range is between about 1.0 and about 2.5 phr, and a more preferred range is between about 1.5 and about 2.0 phr.

The amount of sulfenamide vulcanization accelerator varies with the amount of sulfur used. High sulfur vulcanization processes require less accelerator(s) and vice-versa. Generally, the amount of accelerator ranges from about 0.05 to 6 parts weight per hundred parts of rubber (phr), the preferred range being from about 0.25 to about 3 phr and, more preferably, from about 0.50 to about 2.5 phr.

The rubber compositions of the present invention also may contain conventional compounding ingredients, such as fillers and reinforcing agents (carbon blacks, silicas, clay, talc, $CaCO_3$ and the like), secondary accelerators, activators (zinc oxide, stearic acid, zinc stearate), tackifiers, processing aids, retarders, antioxidants, antiozonants, plasticizing oils and softeners such as naphthenic, aromatic and paraffinic oils.

The various components of the rubber compositions may be mixed into the rubber using an open mill, Banbury mixer, or an extruder, under conditions well-known to those of ordinary skill in the art and exemplified in various of the previously incorporated references and examples set forth below. These compositions can be used in a variety of rubber applications including, for example, tires. The higher scorch safety accelerators of the present invention are particularly suitable for these applications.

The examples which follow are intended as an illustration of certain preferred embodiments of the invention, and no limitation of the invention is implied.

EXAMPLE 1

Preparation of N-(2,3-Dimethylcyclohexyl)-2-benzothiazole sulfenamide (A)

The synthetic method reported by Carr, et al. (*J. Org. Chem.*, 14, 921 (1949), incorporated by reference herein for all purposes) was followed. Mercaptobenzothiazole (MBT), 76 g, was mixed with an aqueous solution of 18.9 g of sodium hydroxide and 250 ml of water for 15 minutes; the mixture was then filtered. To the filtrate was added 114.5 g of 2,3-dimethylcyclohexylamine (Aldrich Chemical Co.) and 640 ml of water, and the mixture was cooled to 9° C. in an ice-water bath. An aqueous sodium hypochlorite solution (5.25%), 770 ml, and 200 ml of a 2N aqueous solution of sulfuric acid were added dropwise simultaneously from two addition funnels to the reaction flask so that the pH of the reaction mixture was kept between 12.2 and 12.7. The mixture was then stirred and kept at 1°–10° C. for 4.5 hours before it was extracted with ether (3×500 ml). The combined ether extracts were washed with cold 1N aqueous hydrochloric acid (3×300 ml), followed by water (1×400 ml) and saturated brine (1×400 ml). The washed organic solution was dried over sodium carbonate, filtered, and the ether stripped off under reduced pressure. The residue, a viscous red oil, weighed 120.0 g. Purification of the crude product by flash chromatography (silica gel) yielded 101.1 g of a waxy material with 98% purity (HPLC); IR (cm$^{-1}$): 3250, 3080, 2930, 1460, 1430, 1030, 1010, 760; $^1$H-NMR (CDCl3): δ 7.79 (t, 2H); 7.38 (m, 1H); 7.25 (t, H); 3.20–3.38 (m, 1H); 2.55–3.08 (m, 1H); 1.10–2.25 (m, 8H); 0.82–1.18 (m, 6H).

EXAMPLE 2

Preparation of N-(2,3-Dimethylcyclohexyl)bis(2-benzothiazole sulfen)amide (B)

The synthetic method reported in previously incorpoated U.S. Pat. No. 2,860,142 was followed. N-(2,3-Dimethylcyclohexyl)-2-benzothiazole sulfenamide, 68.2 g, was mixed with 160 ml of acetic anhydride, and the mixture was heated at 60° C. for 1 hour. After standing at room temperature for 7 hours, the reaction mixture was filtered, and the collected solid was stirred with 1N aqueous sodium hydroxide solution for 2 hours. The aqueous mixture was filtered and the collected solid was washed with water until the filtrate was neutral. The resulting solid weighed 42.7 g (93% yield) after vacuum drying; mp 105°–110° C.; IR (cm$^{-1}$): 3050, 2880, 1410, 980, 750, 725; $^1$H-NMR (CDCl$_3$): δ 7.80–7.98 (m, 2H); 7.31–7.39 (m, 2H); 3.06–3.80 (m, 1H); 1.20–2.40 (m, 8H); 0.82–1.08 (m, 6H).

EXAMPLE 3

Preparation of N-(2,6-Dimethylcyclohexyl)-2-benzothiazole sulfenamide (C)

The procedure of Example 1 was followed, except that 3.14 g of 2,6-dimethylcyclohexylamine hydrochloride (prepared according to the method of Bellucci, et al., Gazz. Chim. Ital. 1969, 99(11), 1217), 1.18 g of sodium hydroxide, 1.57 g of MBT and 16 ml of aqueous sodium hypochlorite solution (5.25%) were used, and no aqueous sulfuric acid was added to the reaction mixture. The dried organic layer was rotary evaporated, affording 1.3 g of a light yellow solid; mp 75°–93° C.; IR (cm$^{-1}$): 3280, 3040, 2860, 1405, 1000, 740; $^1$H-NMR (CDCl$_3$): δ 7.80 (m, 2H); 7.38 (m, 1H); 7.25 (m, 1H); 3.23–3.58 (m, 1H); 2.19–2.68 (m, 1H); 1.40–1.80 (m, 8H); 0.97–1.15 (m, 6H).

EXAMPLE 4

Preparation of N-(α-Methylbenzyl)-2-benzothiazole sulfenamide (D)

The procedure of Example 1 was followed except that 142 g of MBT, 121 g of α-methylbenzylamine (Aldrich Chemical Co.) and 1300 ml of 5.25% sodium hypochlorite were used. The crude sulfenamide was a sticky semi-solid, and therefore after the reaction was completed, the liquid in the reaction flask was decanted and the sticky material was washed with water. The crude product in the flask was then stirred with 1.2 L of ether for 15 minutes and filtered. The filtrate was stripped of ether, and the residue was purified by a silica gel column; mp 50°–53° C.; IR (cm$^{-1}$): 3300, 3200, 3020, 2940, 1460, 1420, 1000, 750, 650; $^1$H-NMR (CDCl$_3$): δ 7.2–7.8 (m, 9H); 4.2 (m, 1H); 3.7 (S, 1H); 2.5 (d, 3H).

EXAMPLE 5

Preparation of Methyl N-(α,α-Dimethylbenzyl) Carbamate (MDBC)

Methyl carbamate, 387 g, and concentrated sulfuric acid, 3.2 g, were heated in a 70° C. oil bath until a clear solution was obtained. To the solution was added 94.3 g of α-methylstyrene, and the reaction mixture was stirred at 65° C. for 3.5 hours before it was poured into 2 L of water. The aqueous mixture was filtered after it had been stirred at room temperature for 15 minutes. The collected solid was washed with water and weighed 125 g after it was air dried; mp 58°–60° C.; IR (cm$^{-1}$): 3320, 1670, 1520, 1280, 1190; $^1$H-NMR (CDCl$_3$): δ 7.2–7.8 (m, 9H); 3.9 (s, 1H); 1.6 (s, 1H).

EXAMPLE 6

Preparation of α,α-Dimethylbenzylamine (DMBA)

A mixture of 125 g of MDBC prepared according to Example 5 and 500 g of 85% potassium hydroxide in 270 ml of methyl cellosolve was heated at reflux temperature for 4 hours. The mixture was then cooled and mixed with 500 ml of methylene chloride and 300 ml of water. The methylene chloride layer was separated and washed with water until its volume remained constant. The methylene chloride layer was dried over potassium carbonate and distilled. α,α-Dimethylbenzylamine, 67 g, was collected; bp 95°–6° C./22 mm Hg; IR (cm$^{-1}$): 3340, 3270, 2950, 1600, 760, 795.

EXAMPLE 7

Preparation of N-(α,α-Dimethylbenzyl)-2-benzothiazole sulfenamide (E)

The procedure of Example 1 was followed except that 119 g of MBT, 110 g of α,α-dimethylbenzylamine and 1113 ml of 5.25% sodium hypochlorite solution were used. The crude product, a solid weighing 167 g, was collected by filtration. The product was stirred with 1.2 L of ether for 15 minutes and then filtered. The filtrate was stripped of ether and the resulting solid was washed with 750 ml of heptane. The washed solid weighed 82 g; mp 88°–90° C.; IR (cm$^{-1}$): 3200, 1450, 1420, 1020, 760, 650; $^1$H-NMR (CDCl$_3$): δ 7.2–7.8 (m, 9H); 3.9 (s, 1H); 2.6 (s, 1H).

EXAMPLE 8

Preparation of 3-Isopropenyl-α,α-dimethylbenzylamine (m-TMA)

The procedure of Example 6 was followed except 259 g of methyl N-(3-isopropenyl-α,α-dimethylbenzyl) carbamate (m-TMU) (prepared in accordance with the procedure set forth in previously incorporated U.S. Pat. No. 4,439,616), 165 g of potassium hydroxide, and 460 ml of methyl cellosolve were used. m-TMA: bp 102°–5° C./1.5 mm Hg;

IR (cm$^{-1}$): 3350, 3280, 2950, 1590, 885, 795; $^1$H-NMR (CDCl$_3$): δ 7.2–7.6 (m, 4H); 5.4 (s, 1H); 5.1 (s, 1H); 2.2 (s, 3H); 2.6 (s, 1H); 2.5 (s, 6H).

EXAMPLE 9

Preparation of N-(3-Isopropenyl-α,α-dimethylbenzyl)-2-benzothiazole sulfenamide (F)

The procedure of Example 1 was followed except that 134 g of MBT, 175 g of 3-isopropenyl-α,α-dimethylbenzylamine (m-TMA, Example 8) and 1500 ml of 5.25% aqueous sodium hypochlorite solution were used. The crude product, a solid, weighed 261 g. After purification with ether and heptane, the product weighed 107 g; mp 93°–5° C.; IR (cm$^{-1}$): 3200, 3020, 1450, 1420, 900, 760; $^1$H-NMR (CDCl$_3$): δ 7.2–7.8 (m, 8H); 5.4 (s, 1H); 5.1 (s, 1H); 3.9 (s, 1H); 2.2 (s, 3H); 1.6 (s, 6H).

EXAMPLE 10

Preparation of N-(α,α-Dimethylbenzyl)bis(2-benzothiazole sulfen)amide (G)

The procedure was similar to that of Example 2. N-(α,α-dimethylbenzyl)-2-benzothiazole sulfenamide, 2.5 g prepared according to the procedure of Example 7, was mixed with 8 g of acetic anhydride, and the mixture was heated in a 70° C. oil bath for 20 hours. The mixture turned to a dark red solution in 15 minutes. The reaction solution was then cooled in a refrigerator for 2 hours, and then filtered. The collected solid was washed with water and air dried. The dry solid weighed 1.3 g; mp 100°–104° C.; IR (cm$^{-1}$): 3020, 2970, 1450, 1420, 1000, 760.

EXAMPLE 11

Preparation of α,α,α,α-Tetramethyl-meta-xylylenediamine (m-TMXDA) and α,α,α,α-Tetramethyl-para-xylylenediamine (p-TMXDA)

m- and p-TMXDA's were prepared by the acid hydrolysis of the corresponding diisocyanates, m- and p-TMXDI's, which in turn were prepared in accordance with the procedure set forth in previously incorporated U.S. Pat. No. 4,439,616.

EXAMPLE 12

Preparation of 2-Benzothiazole sulfenamide

2-Benzothiazole sulfenamide was synthesized from the reaction of 2-mercaptobenzothiazole, ammonia, and sodium hypochlorite in water (previously incorporated *J. Org. Chem.*, 14, 921 (1940)).

EXAMPLE 13

Preparation of α,α,α,α-Tetramethyl-para-xylylene di(2-benzothiazole sulfenamide) (p-TMXDS) (H)

2-Benzothiazole sulfenamide, 1 g, was heated with 10 ml chloroform at 50° C., and the mixture turned to a dark red solution. To this solution was added 0.46 g of p-TMXDA (Example 11), and the reaction mixture was heated at 55° C. for 20 hours. After it cooled to room temperature, the mixture was filtered, and 0.45 g of p-TMXDS was collected; mp 244°–6° C.; IR (cm$^{-1}$): 3240, 1420, 1030, 1010, 760, 730.

EXAMPLE 14

Preparation of α,α,α,α-Tetramethyl-meta-xylylene di(2-benzothiazole sulfenamide) (m-TMXDS) (I)

The procedure of Example 13 was followed except 1 g of 2-benzothiazole sulfenamide, 0.53 g of m-TMXDA (Example 11) and 10 ml of chloroform were used. IR (cm$^{-1}$): 3200, 1590, 1420, 1020, 1000, 750, 720.

Several of the sulfenamide accelerators of the present invention were tested in both synthetic and natural rubber formulations, as described further below. All quantities are in parts per hundred parts of rubber.

SYNTHETIC RUBBER FORMULATIONS—EXAMPLES 15–23

A synthetic rubber masterbatch was prepared by mixing the ingredients of Table 1 in a laboratory Banbury mixer to a dump temperature of 250°–280° F.

TABLE 1

| SYNTHETIC RUBBER Masterbatch (SR) | |
|---|---|
| Component | Parts |
| OE-SBR (Ameripol ® 1712)* | 55.00 |
| E-SBR (Ameripol ® 1500)** | 25.00 |
| Polybutadiene (Takatene ® 1203) | 35.00 |
| Zinc Oxide | 3.00 |
| Stearic Acid | 2.00 |
| Carbon Black | 70.00 |
| Aromatic Oil | 20.00 |
| Antiozonant*** | 2.00 |
| Age-Rite Resin D**** | 2.00 |
| TOTAL: | 214.00 |

*Oil Extended Styrene-Butadiene Rubber
**Emulsion Polymerized Styrene-Butadiene Rubber
***Santoflex ® 13 antiozonant - Monsanto Chemical Co.
****Antioxidant(1,2-Dihydro-2,2,4-trimethylquinoline), product of B.F. Goodrich Company, supplied by R.T. Vanderbilt of Norwalk, CT.

Portions of the synthetic rubber masterbatch were blended with equimolar amounts of sulfur and an accelerator of the invention (as per recipes shown in Table II). MBS, TBBS, CBS and TBSI were used as the reference controls. The different weight amounts of accelerators are due to differences in molecular weights of the individual accelerators. The resulting mixed stocks were sheeted off a two-roll mill for testing.

TABLE II

Synthetic Rubber Compounds (SR Series)

|  | Reference Controls | | | | Accelerators of the Invention | | | | |
| --- | --- | --- | --- | --- | --- | --- | --- | --- | --- |
| Ingredient | Example 15 SR-MBS | Example 16 SR-TBBS | Example 17 SR-CBS | Example 18 SR-TBSI | Example 19 SR-F | Example 20 SR-D | Example 21 SR-E | Example 22 SR-A | Example 23 SR-B |
| Synthetic Rubber Masterbatch | 214.00 | 214.00 | 214.00 | 214.00 | 214.00 | 214.00 | 214.00 | 214.00 | 214.00 |
| Accelerators: | | | | | | | | | |
| MBS | 1.43 | — | — | — | — | — | — | — | — |
| TBBS | — | 1.35 | — | — | — | — | — | — | — |
| CBS | — | — | 1.50 | — | — | — | — | — | — |
| TBSI | — | — | — | 2.29 | — | — | — | — | — |
| F | — | — | — | — | 1.93 | — | — | — | — |
| D | — | — | — | — | — | 1.62 | — | — | — |
| E | — | — | — | — | — | — | 1.70 | — | — |
| A | — | — | — | — | — | — | — | 1.66 | — |
| B | — | — | — | — | — | — | — | — | 2.59 |
| Sulfur | 2.00 | 2.00 | 2.00 | 2.00 | 2.00 | 2.00 | 2.00 | 2.00 | 2.00 |

NATURAL RUBBER FORMULATIONS—EXAMPLES 24–32

The natural rubber masterbatch was similarly prepared by mixing the ingredients of Table III in the Banbury mixer to a dump temperature of 250°–280° F.

TABLE III

Natural Rubber Masterbatch (NR)

| Component | Parts |
| --- | --- |
| Natural Rubber | 100.00 |
| Carbon Black | 55.00 |
| Zinc Oxide | 5.00 |
| Stearic Acid | 0.50 |
| Pine Tar | 5.00 |

TABLE III-continued

Natural Rubber Masterbatch (NR)

| Component | Parts |
| --- | --- |
| BLE-25 (antioxidant)* | 0.75 |
| Antiozonant** | 1.00 |
| TOTAL: | 167.25 |

*Diphenylamine acetone reaction product antioxidant - Uniroyal Chemical Co.
**Santoflex ® 13 antiozonant - Monsanto Chemical Co.

Individual test mixes were prepared by blending portions of the natural rubber masterbatches with the appropriate accelerators using the compound recipes shown in Table IV. As in the case of the synthetic rubber recipes, MBS, TBBS, CBS and TBSI were used as the reference controls.

TABLE IV

Natural Rubber Compounds (NR Series)

|  | Reference Controls | | | | Accelerators of the Invention | | | | |
| --- | --- | --- | --- | --- | --- | --- | --- | --- | --- |
| Ingredient | Example 24 NR-MBS | Example 25 NR-TBBS | Example 26 NR-CBS | Example 27 NR-TBSI | Example 28 NR-F | Example 29 NR-D | Example 30 NR-E | Example 31 NR-A | Example 32 NR-B |
| Natural Rubber Masterbatch | 167.25 | 167.25 | 167.25 | 167.25 | 167.25 | 167.25 | 167.25 | 167.25 | 167.25 |
| Accelerators: | | | | | | | | | |
| MBS | 0.80 | — | — | — | — | — | — | — | — |
| TBBS | — | 0.76 | — | — | — | — | — | — | — |
| CBS | — | — | 0.84 | — | — | — | — | — | — |
| TBSI | — | — | — | 1.28 | — | — | — | — | — |
| F | — | — | — | — | 1.08 | — | — | — | — |
| D | — | — | — | — | — | 0.91 | — | — | — |
| E | — | — | — | — | — | — | 0.95 | — | — |
| A | — | — | — | — | — | — | — | 0.93 | — |
| B | — | — | — | — | — | — | — | — | 1.45 |
| Sulfur | 2.00 | 2.00 | 2.00 | 2.00 | 2.00 | 2.00 | 2.00 | 2.00 | 2.00 |

The performance of the accelerators of Examples 1, 2, 4, 7 and 9 was evaluated by testing the synthetic and natural rubber compositions prepared with those accelerators, (Examples 19–23 and 28–32), for scorch safety, cure rate, and tensile properties. Similar evaluations were made on natural and synthetic rubber compositions containing the reference accelerators, MBS, TBBS, CBS and TBSI (Examples 15–18 and 24–27). Scorch safety was measured by Mooney scorch tests at 138° C. (280° F.) according to ASTM D1646–92. The time in minutes required for a rise of 5 Mooney units above the minimum Mooney viscosity was taken as scorch time ($t_s$). Mooney viscosities were measured at 120° C. (248° F.) as specified in ASTM D1646–92. Stress-strain properties of the cured stocks were tested as specified in ASTM D 412–87. The hardness and Healey rebound of the cured stocks were measured as specified in ASTM D2240–91 and ASTM D1054–91, respectively. The cure characteristics (Oscillating Disc Rheometer ("ODR") data) were determined in accordance with ASTM D2084–91 at two different temperatures with a Monsanto Oscillating Rheometer (1 degree arc), which records development of crosslinks by plotting the increase in torque in rheometer units vs. cure time. The parameters Tmin and Tmax are the minimum and maximum torques before the onset and completion of vulcanization. The parameter $t_{s1}$ is the time required for an increase over Tmin in rheometer torque of 1.0 in lb (1.1 dNm); $t_{c90}$ is the time required in minutes to achieve 90% of the cure or 90% increase in torque due to vulcanization. CRI is the cure rate index which measures the cure rate of the specimen and is obtained by the following expression:

$$CRI = \frac{1}{t_{c90} - t_{s1}} \times 100$$

The higher the CRI, the faster the cure rate. The results of these tests are summarized in Tables V and VI.

Tensile properties were measured in accordance with ASTM D412–92 (cross head speed, 20 in/min; gauge length, 1 in; stress range, 5000 lbf/in$^2$; strain range, 1000%).

TABLE V

ODR and Mooney Scorch Data
Synthetic Rubber Components

| | Reference Controls | | | | Accelerators of the Invention | | | | |
| --- | --- | --- | --- | --- | --- | --- | --- | --- | --- |
| PROPERTY | Example 15 SR-MBS | Example 16 SR-TBBS | Example 17 SR-CBS | Example 18 SR-TBSI | Example 19 SR-F | Example 20 SR-D | Example 21 SR-E | Example 22 SR-A | Example 23 SR-B |
| ODR @ 320° F. (160° C.) | | | | | | | | | |
| Tmax | 33.6 | 33.2 | 32.9 | 38.0 | 31.4 | 31.5 | 31.5 | 32.0 | 35.5 |
| Tmin | 7.1 | 6.8 | 6.8 | 7.4 | 6.7 | 6.9 | 6.7 | 6.4 | 6.5 |
| $t_{s1}$ | 7.61 | 6.3 | 6.0 | 6.6 | 6.9 | 6.8 | 7.0 | 6.9 | 6.5 |
| $t_{c90}$ | 6.8 | 13.9 | 12.8 | 17.1 | 18.6 | 16.0 | 18.8 | 14.9 | 17.9 |
| CRI | 10.87 | 13.16 | 14.71 | 9.52 | 8.55 | 10.87 | 8.47 | 12.50 | 8.77 |
| REV* | | | | | | | | | |
| (in lb/min.) | 0.04 | 0.04 | 0.04 | 0.04 | 0.00 | 0.00 | 0.00 | 0.04 | 0.00 |
| (dNm/min.) | 0.05 | 0.05 | 0.05 | 0.05 | | | | 0.05 | |
| Mooney Viscosity @ 248° F. (120° C.) ML 1 + 4** | | | | | | | | | |
| (in lb) | 46.96 | 46.24 | 46.08 | 45.52 | 45.63 | 45.91 | 47.02 | 45.97 | 46.08 |
| (dNm) | 53.06 | 52.25 | 52.07 | 51.44 | 51.56 | 51.88 | 53.13 | 51.95 | 52.07 |
| Mooney Scorch @ 280° F. (138° C.) $t_s$ | 23.17 | 19.08 | 17.33 | 24.08 | 23.42 | 21.58 | 23.92 | 21.58 | 25.17 |
| TENSILE | | | | | | | | | |
| STRAIN @ BR*** | 536% | 494% | 550% | 476% | 641% | 564% | 561% | 469% | 375% |
| STRESS @ BR | | | | | | | | | |
| (lbf/in$^2$) | 2300 | 1990 | 2260 | 2400 | 2520 | 2110 | 2130 | 1810 | 1580 |
| (MPa) | 15.9 | 13.7 | 15.6 | 16.5 | 17.4 | 14.5 | 14.7 | 12.5 | 10.9 |
| 300% STRESS | | | | | | | | | |
| (lbf/in$^2$) | 996 | 989 | 968 | 1331 | 846 | 858 | 869 | 955 | 1180 |
| (MPa) | 6.9 | 6.8 | 6.7 | 9.2 | 5.8 | 5.9 | 6.0 | 6.6 | 8.1 |
| HARDNESS: | | | | | | | | | |
| @ Room Temp. | 69.8 | 69.7 | 70.9 | 73.3 | 69.1 | 70.2 | 68.7 | 69.6 | 71.8 |
| @ 212° F. (100° C.) | 58.7 | 59.0 | 59.2 | 63.3 | 58.6 | 58.0 | 58.3 | 58.1 | 61.0 |
| REBOUND: | | | | | | | | | |
| @ Room Temp. | 29.5% | 29.8% | 29.2% | 30.0% | 29.0% | 29.0% | 29.3% | 29.6% | NA |
| @ 212° F. (100° C.) | 27.4% | 48.4% | 46.5% | 50.9% | 45.4% | 45.2% | 46.6% | 47.0% | NA |

*Cure reversion
**ML 1 + 4—Mooney viscosity M measured using a large rotor L with a preheat time of 1 minute and viscosity measurement after 4 minutes of the preheat period
***BR—break

TABLE VI

ODR and Mooney Scorch Data
Natural Rubber Components

| | Reference Controls | | | | Accelerators of the Invention | | | | |
|---|---|---|---|---|---|---|---|---|---|
| PROPERTY | Example 24 NR-MBS | Example 25 NR-TBBS | Example 26 NR-CBS | Example 27 NR-TBSI | Example 28 NR-F | Example 29 NR-D | Example 30 NR-E | Example 31 NR-A | Example 32 NR-B |
| ODR @ 302° F. (150° C.) | | | | | | | | | |
| Tmax | 35.7 | 38.1 | 37.5 | 40.8 | 33.3 | 33.5 | 33.1 | 36.7 | 39.8 |
| Tmin | 8.0 | 7.8 | 8.0 | 8.4 | 8.3 | 8.2 | 8.5 | 8.3 | 8.2 |
| $t_{s1}$ | 5.7 | 6.3 | 5.9 | 5.8 | 6.7 | 5.9 | 6.3 | 6.5 | 5.6 |
| $t_{c90}$ | 18.4 | 16.4 | 14.0 | 18.4 | 20.1 | 16.4 | 20.3 | 15.8 | 17.1 |
| CRI | 7.88 | 9.90 | 12.35 | 7.94 | 7.46 | 9.52 | 7.14 | 10.76 | 8.70 |
| REV* | | | | | | | | | |
| (in lb/min.) | 0.12 | 0.13 | 0.13 | 0.11 | 0.10 | 0.11 | 0.10 | 0.13 | 0.12 |
| (dNm/min.) | 0.14 | 0.15 | 0.15 | 0.12 | 0.11 | 0.12 | 0.11 | 0.15 | 0.14 |
| Mooney Viscosity @ 248° F. (120° C.) | | | | | | | | | |
| ML 1 + 4** | | | | | | | | | |
| (in lb) | 47.30 | 53.52 | 54.30 | 55.08 | 56.02 | 54.30 | 56.52 | 55.41 | 55.30 |
| (dNm) | 53.44 | 60.48 | 61.36 | 62.24 | 63.30 | 61.36 | 63.87 | 62.61 | 62.49 |
| Mooney Scorch @ 280° F. (138° C.) | 11.75 | 11.42 | 10.08 | 10.75 | 12.17 | 10.67 | 11.83 | 11.33 | 9.75 |
| $t_s$ | | | | | | | | | |
| TENSILE | | | | | | | | | |
| STRAIN @ BR*** | 543% | 522% | 535% | 533% | 533% | 547% | 530% | 534% | 440% |
| STRESS @ BR | | | | | | | | | |
| (lbf/in$^2$) | 3620 | 3740 | 3870 | 4170 | 3390 | 3430 | 3320 | 2820 | 3210 |
| (MPa) | 25.0 | 25.8 | 26.7 | 28.8 | 23.4 | 23.6 | 22.9 | 19.4 | 22.1 |
| 300% STRESS | | | | | | | | | |
| (lbf/in$^2$) | 1635 | 1836 | 1823 | 2018 | 1537 | 1517 | 1490 | 1793 | 1945 |
| (MPa) | 11.3 | 12.7 | 12.6 | 13.9 | 10.6 | 10.5 | 10.3 | 12.4 | 13.4 |
| HARDNESS: | | | | | | | | | |
| @ Room Temp. | 66.8 | 68.9 | 64.7 | 66.0 | 65.9 | 64.1 | 65.6 | 65.8 | 64.8 |
| @ 212° F. (100° C.) | 59.1 | 61.4 | 58.7 | 59.9 | 59.0 | 55.3 | 58.8 | 60.0 | 59.3 |
| REBOUND: | | | | | | | | | |
| @ Room Temp. | 44.0% | 43.8% | 45.4% | 45.8% | 43.6% | 43.4% | 43.4% | 44.5% | 46.8% |
| @ 212° F. (100° C.) | 54.1% | 55.3% | 56.8% | 57.8% | 54.2% | 52.4% | 53.4% | 56.0% | 59.4% |

*Cure reversion
**ML 1 + 4—Mooney viscosity M measured using a large rotor L with a preheat time of 1 minute and viscosity measurements after 4 minutes of the preheat period
***BR—break The Mooney scorch tests on the synthetic and natural rubber formulations summarized in Tables V and VI indicate that several of the accelerators of the present invention are superior in scorch safety (higher scorch time, $t_s$) relative to the commercial non-nitrosamine controls CBS and TBBS but surprisingly equivalent or nearly so compared to the best industry standard, MBS. Unlike MBS which is based on morpholine, a secondary amine, and which produces a stable nitrosamine, the accelerators of the present invention are all derived from the primary amines and are expected not to produce stable nitrosamines.

The accelerators of the present invention on average display acceptable cure rates (CRI's at 320° F. for SR series and 302° F. for NR series) and do not require the addition of auxiliary modifiers. Other properties such as modulus (300% stress), hardness and rebound all appear to be roughly comparable.

Many modifications and variations can be made to the embodiments specifically mentioned herein without departing substantially from the concept of the present invention. Accordingly, it should be clearly understood that the preferred form of the invention described herein is exemplary only, and is not intended as a limitation on the scope thereof.

What is claimed is:

1. A benzothiazole sulfenamide compound represented by Formula (I)

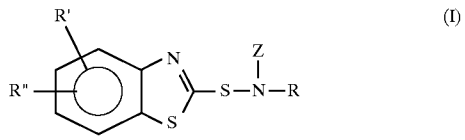

wherein Z is selected from the group consisting of hydrogen and a sulfobenzothiazole group represented by the Formula (II)

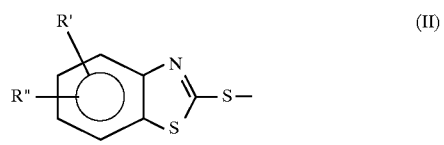

wherein each R' and R" is independently selected from the group consisting of hydrogen and $C_1$–$C_6$ alkyl; and wherein R is Formula (i) or Formula (ii)

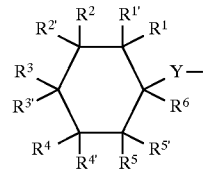

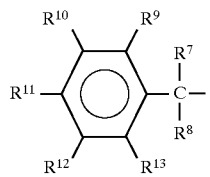

wherein in Formula (i)
Y is either a direct bond or a group of the formula $-[(R^{14})(R^{15})C-]-$, wherein $R^{14}$ and $R^{15}$ are independently hydrogen or $C_1-C_6$ alkyl,
$R^1$, $R^{1'}$, $R^2$, $R^{2'}$, $R^3$, $R^{3'}$, $R^4$, $R^{4'}$, $R^5$, $R^{5'}$ and $R^6$ are each independently hydrogen or $C_1-C_6$ alkyl, and one of $R^2$, $R^{2'}$, $R^3$, $R^{3'}$, $R^4$, $R^{4'}$ may optionally further be Formula (iii)

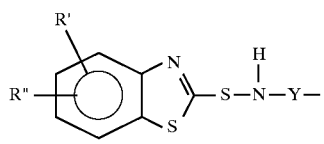

wherein R', R" and Y are as defined above,
with the proviso that at least two of $R^1$ through $R^6$ are $C_1-C_6$ alkyl; and
wherein in the Formula (ii),
$R^7$ is a $C_1-C_6$ alkyl,
$R^8$ is hydrogen or $C_1-C_6$ alkyl, and
$R^9$, $R^{10}$, $R^{11}$, $R^{12}$ and $R^{13}$ are each independently hydrogen or $C_1-C_6$ alkyl, with the proviso that one of $R^{10}$, $R^{11}$, $R^{12}$ may optionally further be selected from the group consisting of $CH_2-CH-$, $CH_2=C(CH_3)-$, $CH_2=CH-CH_2-$, $CH_2=C(CH_3)CH_2-$, and a group of the formula (iii), and with the proviso that when Z is a sulfobenzothiazole of Formula (II), one of $R^{10}$, $R^{11}$ or $R^{12}$ is $C_2-C_6$ alkyl, $CH_2=CH-$, $CH_2=C(CH_3)-$, $CH_2=CH-CH_2-$, $CH_2=C(CH_3)CH_2-$, or a group of the formula (iii).

2. The benzothiazole sulfenamide compound according to claim 1 wherein Z is H and R is a group represented by Formula (iv)

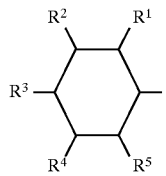

wherein $R^1$, $R^2$, $R^3$, $R^4$, and $R^5$ are independently selected from the group consisting of hydrogen and $C_1-C_6$ alkyl, with the proviso that at least two of $R^1$ through $R^5$ are $C_1-C_6$ alkyl.

3. The benzothiazole sulfenamide compound according to claim 2, wherein $R^1$, $R^2$, $R^3$, $R^4$, and $R^5$ are independently hydrogen or methyl, provided that at least two of $R^1$ through $R^5$ are methyl.

4. The benzothiazole sulfenamide compound according to claim 3, selected from the group consisting of N-(2,3-dimethylcyclohexyl)-2-benzothiazole sulfenamide, N-(2,4-dimethylcyclohexyl)-2-benzothiazole sulfenamide, N-(2,5,-dimethylcyclohexyl)-2-benzothiazole sulfenamide and N-(2,6-dimethylcyclohexyl)-2-benzothiazole sulfenamide.

5. The benzothiazole sulfenamide compound according to claim 1, wherein Z is the sulfobenzothiazole group of Formula (II) and R is a group represented by Formula (iv)

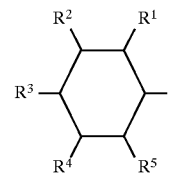

wherein $R^1$, $R^2$, $R^3$, $R^4$, and $R^5$ are independently hydrogen or $C_1-C_6$ alkyl, with the proviso that at least two of $R^1$ through $R^5$ are $C_1-C_6$ alkyl.

6. The benzothiazole sulfenamide compound according to claim 5, wherein $R^1$, $R^2$, $R^3$, $R^4$, and $R^5$ are independently hydrogen or methyl, provided that at least two of $R^1$ through $R^5$ are methyl.

7. The benzothiazole sulfenamide compound according to claim 6, selected from the group consisting of N-(2,3-dimethylcyclohexyl)bis(2-benzothiazole sulfen)amide, N-(2,4-dimethylcyclohexyl)bis(2-benzothiazole sulfen) amide, N-(2,5-dimethylcyclohexyl)bis(2 -benzothiazole sulfen)amide and N-(2,6-dimethylcyclohexyl)bis(2-benzothiazole sulfen)amide.

8. The benzothiazole sulfenamide compound according to claim 1, wherein Z=H and R is a group represented by Formula (v)

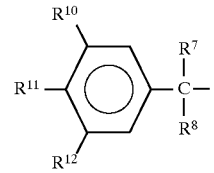

wherein $R^7$ is a $C_1-C_6$ alkyl, $R^8$ is hydrogen or $C_1-C_6$ alkyl, and $R^{10}$, $R^{11}$ and $R^{12}$ are hydrogen, with the proviso that one of $R^{10}$, $R^{11}$ and $R^{12}$ may optionally be $CH_2=CH-$, $CH_2=C(CH_3)-$, $CH_2=CH-CH_2-$, or $CH_2=C(CH_3)CH_2-$.

9. The benzothiazole sulfenamide compound according to claim 8, wherein $R^7$ is methyl, $R^8$ is hydrogen or methyl, and two of $R^{10}$, $R^{11}$ and $R^{12}$ are hydrogen and the other is hydrogen or isopropenyl.

10. The benzothiazole sulfenamide compound according to claim 9, selected from the group consisting of N-(α-methylbenzyl)-2-benzothiazole sulfenamide, N-(α,α-dimethylbenzyl)-2-benzothiazole sulfenamide, N-(3-isopropenyl-α,α-dimethylbenzyl)-2-benzothiazole sulfenamide, and N-(4-isopropenyl-α,α-dimethylbenzyl)-2-benzothiazole sulfenamide.

11. The benzothiazole sulfenamide compound according to claim 1, wherein Z is the sulfobenzothiazole group (II), and R is a group represented by Formula (v)

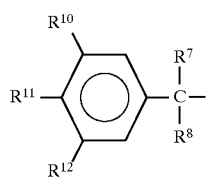

wherein $R^7$ is a $C_1$–$C_6$ alkyl, $R^8$ is hydrogen or $C_1$–$C_6$ alkyl, and $R^{10}$, $R^{11}$ and $R^{12}$ are hydrogen, with the proviso that one of $R^{10}$, $R^{11}$ and $R^{12}$ is $C_2$–$C_6$ alkyl, $CH_2$=CH—, $CH_2$=C($CH_3$)—, $CH_2$=CH—$CH_2$—, or $CH_2$=C($CH_3$)$CH_2$—.

12. The benzothiazole sulfenamide compound according to claim 11, wherein $R^7$ is methyl, $R^8$ is hydrogen or methyl, and two of $R^{10}$, $R^{11}$ and $R^{12}$ are hydrogen and the other is isopropenyl.

13. The benzothiazole sulfenamide compound according to claim 12, selected from the group consisting of N-(3-isopropenyl-α,α-dimethylbenzyl)bis(2-benzothiazole sulfen)amide, and N-(4-isopropenyl-α,α-dimethylbenzyl)bis(2-benzothiazole sulfen)amide.

14. A benzothiazole sulfenamide compound represented by the Formula (I)

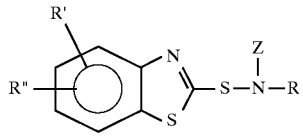

wherein Z is hydrogen, and
R is a group represented by the Formula (v)

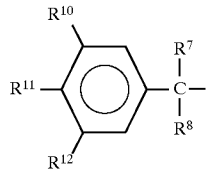

wherein $R^7$ is a $C_1$–$C_6$ alkyl,
$R^8$ is selected from the group consisting of hydrogen and $C_1$–$C_6$ alkyl, and two of $R^{10}$, $R^{11}$ and $R^{12}$ are hydrogen, and the other is represented by a group of the formula (vi)

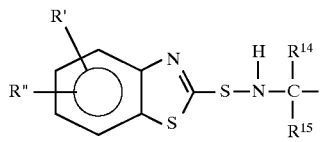

wherein $R^{14}$ is a $C_1$–$C_6$ alkyl, and $R^{15}$ is selected from the group consisting of hydrogen and $C_1$–$C_6$ alkyl; and
wherein each R' and R" is independently selected from the group consisting of hydrogen and $C_1$–$C_6$ alkyl.

15. The benzothiazole sulfenamide compound according to claim 14, wherein $R^7$ is methyl, $R^8$ is hydrogen or methyl, $R^{14}$ is methyl and $R^{15}$ is hydrogen or methyl.

16. The benzothiazole sulfenamide compound according to claim 15, selected from the group consisting of α,α,α',α'-tetramethyl-para-xylylene di(benzothiazole sulfenamide) and α,α,α',α'-tetramethyl-meta-xylylene di(benzothiazole sulfenamide).

17. A benzothiazole sulfenamide compound represented by Formula (I)

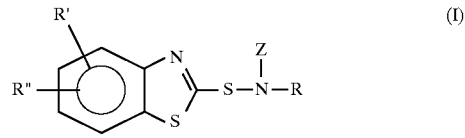

wherein Z is hydrogen or a sulfobenzothiazole group represented by the Formula (II)

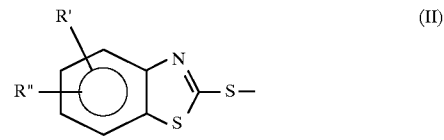

wherein each of R' and R" is independently hydrogen or $C_1$–$C_6$ alkyl; and
wherein R is a group represented by Formula (ii)

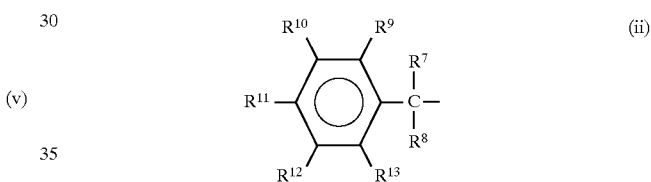

wherein in the Formula (ii),
$R^7$ is a $C_1$–$C_6$ alkyl,
$R^8$ is hydrogen or $C_1$–$C_6$ alkyl, and
$R^9$, $R^{10}$, $R^{11}$, $R^{12}$ and $R^{13}$ are each independently hydrogen or $C_1$–$C_6$ alkyl, with the proviso that at least one of $R^{10}$, $R^{11}$ or $R^{12}$ is $C_2$–$C_6$ alkyl, $CH_2$=CH—, $CH_2$=C($CH_3$)—, $CH_2$=CH—$CH_2$—, $CH_2$=C($CH_3$)$CH_2$—, or a group of the formula (iii)

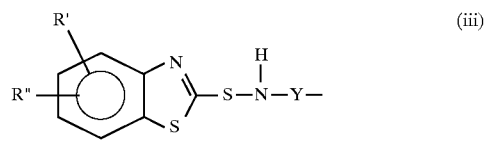

wherein R', R" and Y are as defined above.

* * * * *

UNITED STATES PATENT AND TRADEMARK OFFICE
CERTIFICATE OF CORRECTION

PATENT NO. : 5,840,908

DATED : November 24, 1998

INVENTOR(S) : SINGH et al.

It is certified that error appears in the above-identified patent and that said Letters Patent is hereby corrected as shown below:

Column 17, line 40, "$CH_2$-CH" should read--

$CH_2$=CH-, --.

Signed and Sealed this

Twentieth Day of April, 1999

Attest:

Q. TODD DICKINSON

*Attesting Officer*   Acting Commissioner of Patents and Trademarks